United States Patent [19]

Dilmanian et al.

[11] Patent Number: 5,583,343
[45] Date of Patent: Dec. 10, 1996

[54] FLEXIBLE NUCLEAR MEDICINE CAMERA AND METHOD OF USING

[75] Inventors: F. Avraham Dilmanian, Yaphank; Samuel Packer, Great Neck; Daniel N. Slatkin, Sound Beach, all of N.Y.

[73] Assignee: Associated Universities, Inc., Washington, D.C.

[21] Appl. No.: 506,816

[22] Filed: Jul. 25, 1995

[51] Int. Cl.$^6$ .................................................. G03B 42/04
[52] U.S. Cl. ........................................ 250/475.2; 378/184
[58] Field of Search ........................ 250/475.2; 378/184, 378/205

[56] References Cited

U.S. PATENT DOCUMENTS

| | | | |
|---|---|---|---|
| 2,371,843 | 3/1945 | Powers | 378/184 |
| 3,952,204 | 4/1976 | Davis et al. | 378/184 |
| 5,077,479 | 12/1991 | de la Barre et al. | 250/363.1 |
| 5,105,086 | 4/1992 | Pierfitte et al. | 250/363.08 |
| 5,151,598 | 9/1992 | Denen | 250/336.1 |
| 5,155,365 | 10/1992 | Cann et al. | 250/363.02 |
| 5,173,608 | 12/1992 | Motomura et al. | 250/363.09 |

FOREIGN PATENT DOCUMENTS

| | | |
|---|---|---|
| 2006059 | 12/1969 | France . |
| 59-38736 | 3/1984 | Japan ..................................... 378/184 |
| 3-119342 | 5/1991 | Japan ..................................... 378/184 |
| 7804536 | 4/1978 | Netherlands . |

OTHER PUBLICATIONS

Anonymous, "Flexible pouch provided with a stiffening means and used directly for the exposure of an X– or γ–ray sensitive material." *Research Disclosure* #13561 (Jul. 1975) p. 61.

*Primary Examiner*—Constantine Hannaher
*Attorney, Agent, or Firm*—Margaret C. Bogosian

[57] ABSTRACT

A nuclear medicine camera 10 and method of use photographically record radioactive decay particles emitted from a source, for example a small, previously undetectable breast cancer, inside a patient. The camera 10 includes a flexible frame 20 containing a window 22, a photographic film 24, and a scintillation screen 26, with or without a gamma-ray collimator 34. The frame 20 flexes for following the contour of the examination site on the patient, with the window 22 being disposed in substantially abutting contact with the skin of the patient for reducing the distance between the film 24 and the radiation source inside the patient. The frame 20 is removably affixed to the patient at the examination site for allowing the patient mobility to wear the frame 20 for a predetermined exposure time period. The exposure time may be several days for obtaining early qualitative detection of small malignant neoplasms.

19 Claims, 6 Drawing Sheets

FLEXIBLE NUCLEAR MEDICINE CAMERA AND METHOD OF USING

This invention was made with Government support under contract number DE-AC02-76CH00016, between the U.S. Department of Energy and Associated Universities, Inc. The Government has certain rights in the invention.

BACKGROUND OF THE INVENTION

The present invention relates generally to nuclear medicine, and, more specifically, to a camera for detecting shallow lesions or tumors identified by a radioactive agent.

Diagnostic imaging with photons (i.e. X-rays or gamma rays) is divided into two categories: Transmission and emission. In transmission imaging, such as common x-ray imaging, the examination site such as the chest is positioned close to or adjacent to a flat x-ray film plate assembly. A suitable point x-ray source is temporarily provided behind the patient so that x-rays pass through the patient to the film plate. The film plate typically includes a rigid frame in which is supported a flat photographic film with one or two conventional scintillation screens which emit light when bombarded with x-rays for forming an exposure image on the film. The film is conventionally developed so that the recorded image may be visually analyzed by a radiologist to determine whether or not there is an abnormality such as a tumor or other lesion therein.

On the other hand, nuclear radiation is used for detecting various anomalies within the human body through emission of gamma rays from the body. In this method, a gamma-emitting radioactive isotope in a pharmaceutical agent is administered to the patient either orally or by injection, with the agent being specifically selected for targeting a selected organ or lesion such as a cancerous tumor in the eye, thyroid, or trunk, for example. The patient then lies down on a table or sits down in a chair in front of a gamma camera which detects the gamma radiation from the patient, or more particularly from the examination site of interest in the patient, analyzes the data, and provides an analysis in the form of a computer produced digital image of the radiation source. In this way location and configuration of the tumor may be identified in the patient. The gamma camera is typically quite large and heavy, and is used for a relatively short time on the order of tens of minutes to provide accurate and detailed quantitative data regarding the tumor.

Unlike the simple chest x-ray, conventional gamma cameras use sophisticated radiation detector heads having suitable scintillators therein and corresponding photomultiplier arrays for creating the electrical signals or pulses from the radiation emitted from the examination site. These signal or pulses are then analyzed mathematically using high-speed processors so that a virtual image of the source distribution will be produced. Emission imaging is also done in the tomography mode, in which multiple gamma cameras rotate around the patient.

SUMMARY OF THE INVENTION

A nuclear medicine camera and method of use photographically record radioactive decay particles emitted from a source inside a patient. The camera includes a flexible frame containing a window, a photographic film, and a scintillation screen. The frame flexes for following the contour of the examination site on the patient, with the window being disposed adjacent the examination site for reducing the distance between the film and the radiation source inside the patient. The frame is removably affixed to the patient at the examination site for allowing the patient mobility to wear the frame for a predetermined period of exposure. The exposure time may be relatively long for obtaining early qualitative detection of small tumors.

BRIEF DESCRIPTION OF THE DRAWINGS

The invention, in accordance with preferred and exemplary embodiments, together with further objects and advantages thereof, is more particularly described in the following detailed description taken in conjunction with the accompanying drawings in which.

DESCRIPTION OF THE PREFERRED EMBODIMENT(S)

Figure 1:
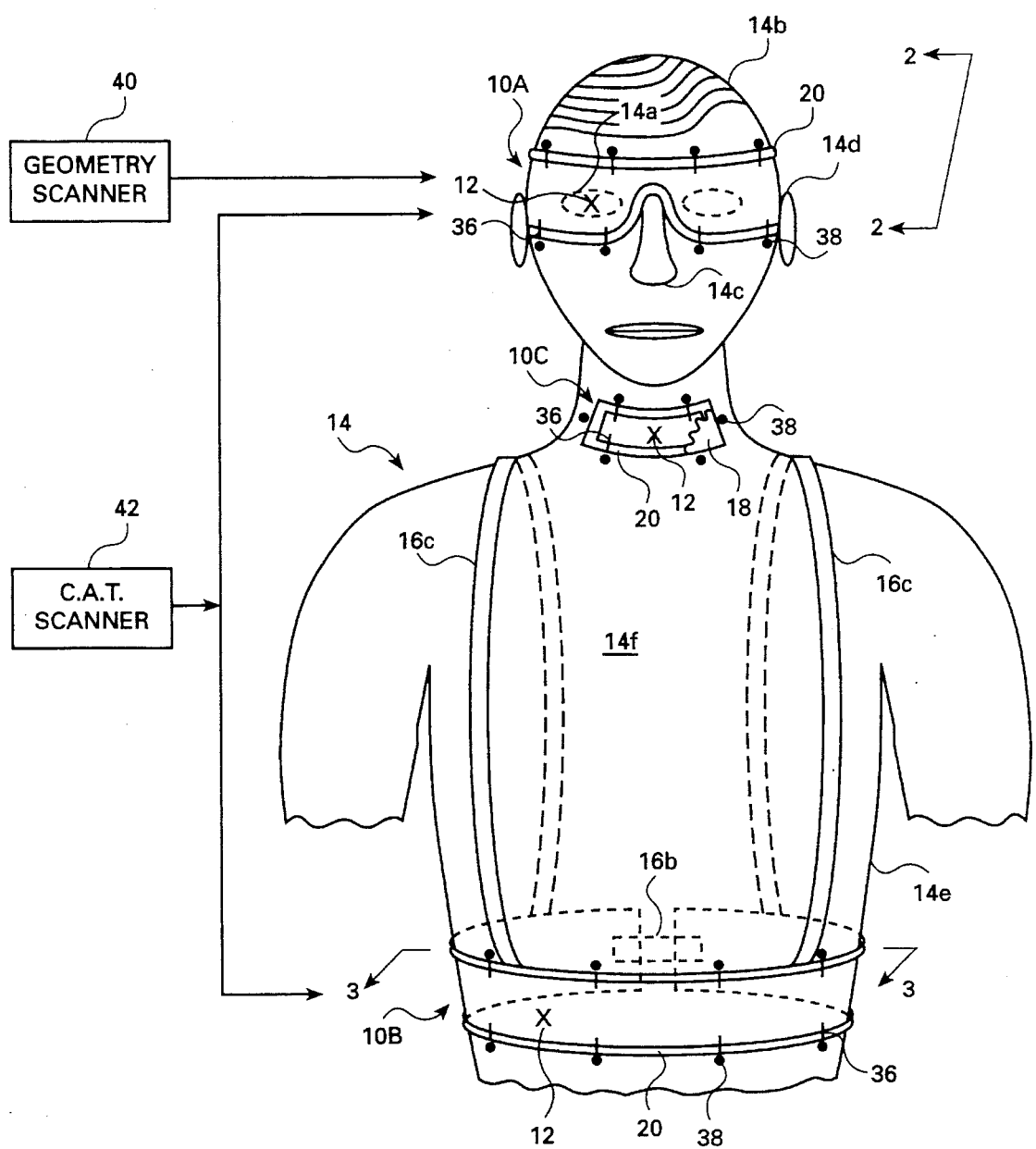
FIG. 1 is a schematic representation of several embodiments of a flexible nuclear medicine camera affixed to a patient at various examination sites for imaging radioactive decay particles in accordance with the present invention.

Illustrated in FIG. 1 are three generally similar embodiments of nuclear medicine cameras 10A, 10B, and 10C in accordance with the present invention for photographically recording radioactive decay particles or rays emitted from a radioactive site or source 12 inside the body of a human subject or patient 14 shown at various exemplary locations.

Figure 2:
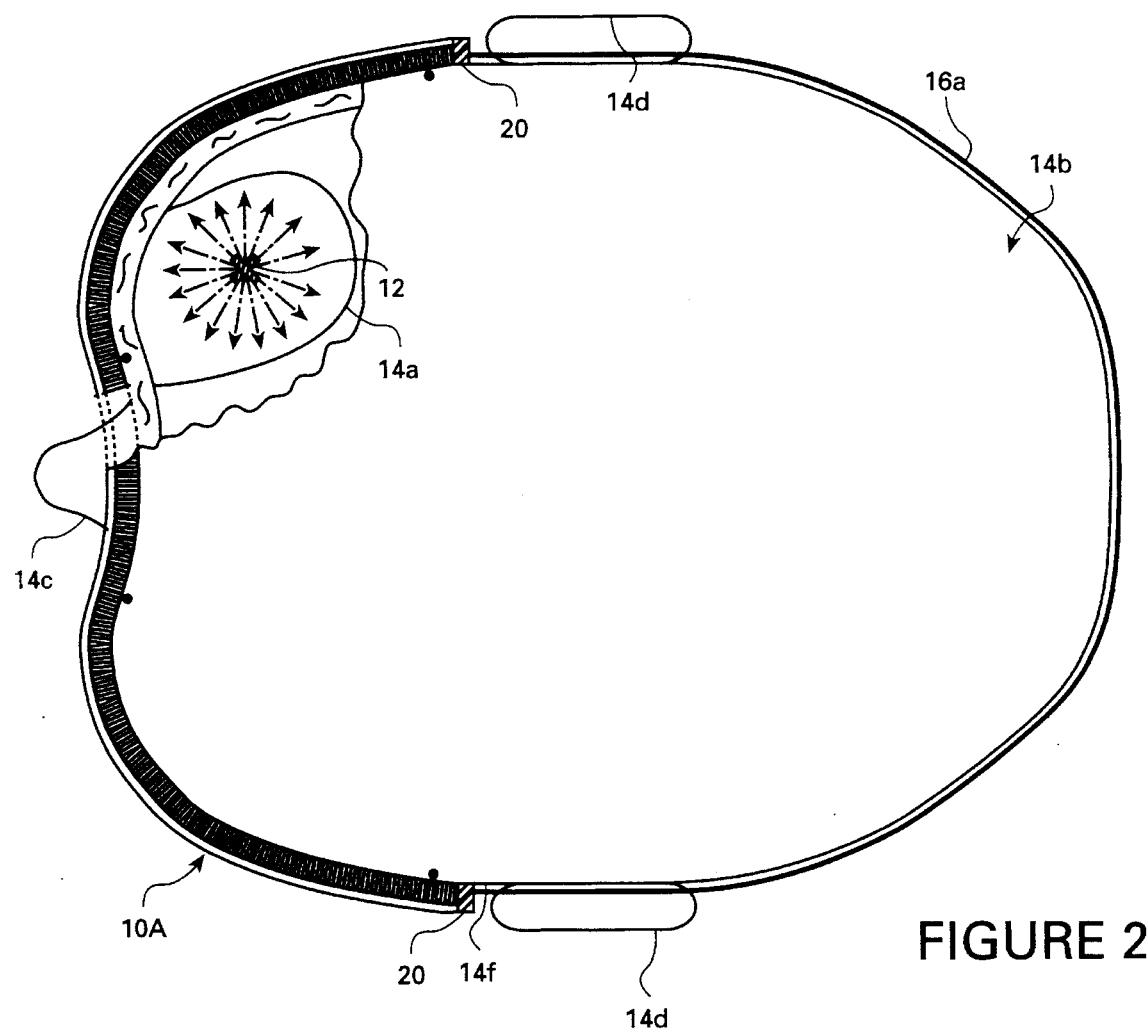
FIG. 2 is a top view of the patient's head, partly in section along line 2–2 of FIG. 1, illustrating one embodiment of the camera in the form of a blindfold worn across both eyes of the patient and wrapped around the head thereof for detecting an eye tumor.

In one exemplary embodiment, the camera is in the form of a blindfold 10A wearable by the patient 14 over at least one eye 14a thereof forming one examination site. The blindfold camera 10A is suitably removably affixed to the head 14b of the patient 14 by being wrapped substantially around the head 14, and may be positioned over the nose 14c and ears 14d in a manner similar to conventional eye glasses, or continuous headband, or joined together at opposite ends thereof by a first strap 16a as shown in FIG. 2 which wraps around the back of the head 14b. The blindfold camera 10a may also be configured as a single eye patch over only one of the eyes if desired.

Figure 3:
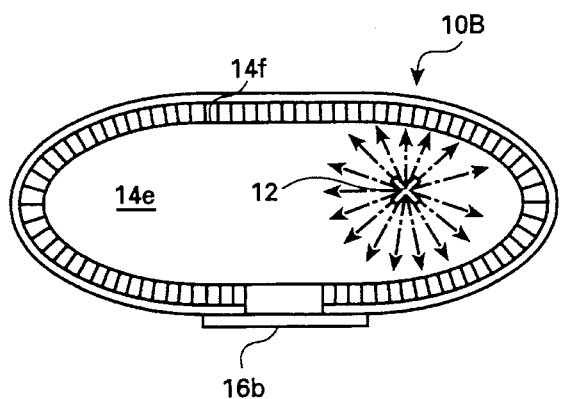
FIG. 3 is a sectional view of another embodiment of a camera in the form of a belt worn around the chest or the abdomen of the patient and taken along line 3–3 in FIG. 1 for recording a tumor in one of the organs therein.

FIG. 1 also illustrates the camera in the form of a belt 10B wearable by the patient 14 around a selected portion of the trunk 14e thereof which forms the respective examination site. The belt camera 10B may be positioned at any elevation around the trunk 14e from the abdomen to the thorax as desired. The belt camera 10B is removably affixed to the patient's trunk 14e by a second strap 16b, shown in more particularity in FIG. 3, which joins the opposite ends of the belt camera 10B together. A pair of third or suspender straps 16c may be provided over both shoulders of the patient 14 and suitably joined to the belt camera 10B for additionally supporting the belt camera 10B on the patient's trunk 14e.

FIG. 1 also illustrates a third embodiment of the camera in the form of a simple patch 10C which is wearable by the patient 14 over any selected area of the skin 14f. The camera patch 10C is suitably removably affixed to the patient's skin 14f by a suitable adhesive 18 in the exemplary form of double sided tape. In the exemplary embodiment illustrated in FIG. 1, the patch camera 10C is affixed on the patient's neck over the thyroid gland.

These exemplary embodiments of the camera 10A–C are all generally similar in construction but are each specifically tailored in shape for being worn by the patient at any desired location on the patient's skin 14f for photographically recording radioactive decay particles or rays emitted from the radioactive source 12 wherever it may be located inside the patient 14.

Figure 4:
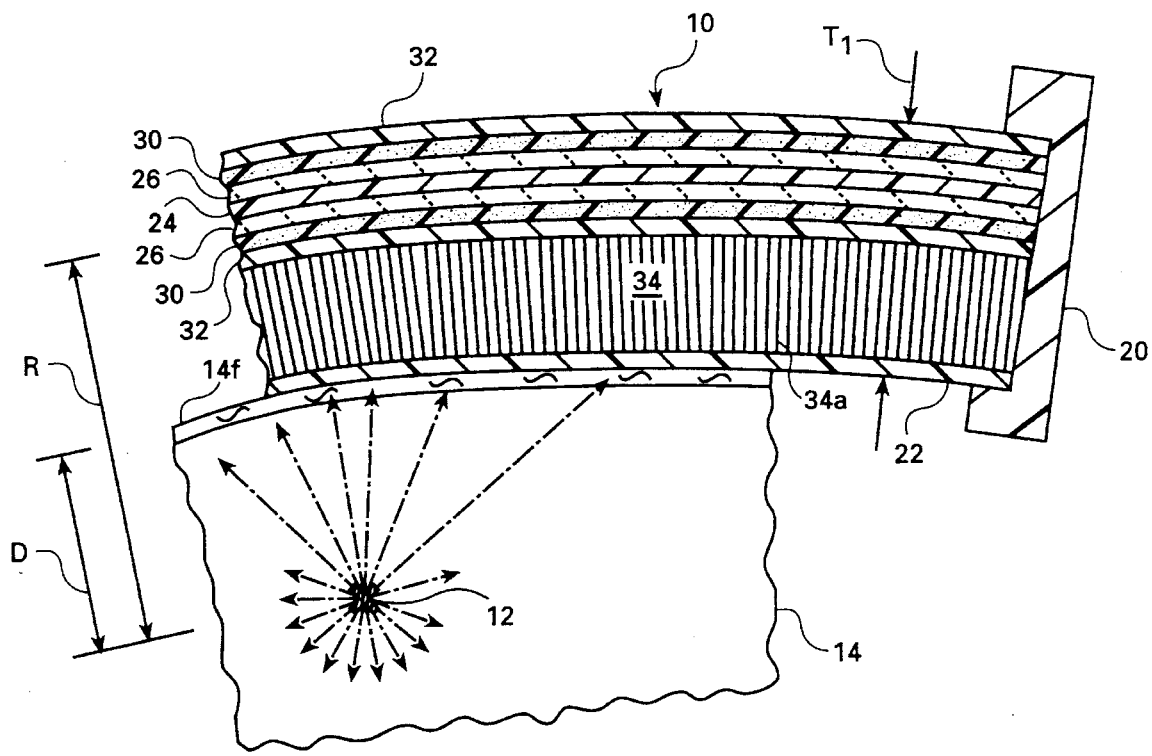
FIG. 4 is a partly sectional view of a portion of a flexible nuclear medicine camera in accordance with one embodiment of the present invention which is representative of each of the several camera embodiments illustrated in FIG. 1 disposed adjacent to the skin of the subject for photographically recording radioactive decay particles emitted from a tumor source inside the patient and passing through a collimator.

FIG. 4 illustrates an exemplary portion of the patient 14 with the radioactive source 12 located at a depth D below the surface of the skin 14f thereof and is representative of any location on the patient's body. The nuclear medicine camera is designated generally by the numeral 10 in FIG. 4, only a representative portion of which is illustrated, and is representative also of the several embodiments 10A, 10B, and 10C. The camera 10 includes a flexible housing or frame 20 which contains or supports among other things a camera window 22, an unexposed radiographic or photographic film 24, and a scintillation screen 26 disposed adjacent to the film 24 for converting the primary radiation into secondary radiation to expose the film 24. The scintillation screen 26 emits the secondary radiation such as visible light to form a photographic exposure image 28 (see FIG. 6) on the film 24 upon reception through the window 22 of the primary radiation or radioactive decay particles from the source 12 inside the patient 14.

A significant feature of the present invention is that the camera frame 20, including its supported window 22, film 24, and screen 26, are all preferably flexible for following the arcuate contour of the selected portion or examination site of the patient, 14 so that the window 22 is disposed adjacent to and in substantially abutting contact or near-contact with the skin 14f of the patient 14 adjacent to the radiation source 12. The camera may also be positioned next to bone or inside the patient if desired.

At the beginning of the examination, the exact location of the radioactive source 12 is not known. As well known in the prior art, testing commences by administering either orally or by injection a suitable radioactive agent into the patient 14 which is selected for accumulating at one or more sources 12 inside the patient 14 so that radioactive decay particles may be emitted therefrom in order to pinpoint the location of the source in the patient 14. In the example illustrated in FIG. 1 and 2, the radioactive source 12 is in the exemplary form of an eye tumor in the patient's right eye, and after administering the radioactive agent in the subject 14 it accumulates at the site of the eye tumor, which is the respective radiation source 12 in this embodiment. In order to locate the radiation source 12 in accordance with the prior art, a typical gamma camera is used which has movable radiation detector heads that detect the radiation emitted from the source 12 to quantitatively determine the precise location and configuration of the source, i.e. the tumor. The conventional gamma camera is large, heavy, sometimes immobile, and may only be used for a relatively short time on the order of tens of minutes for each patient in view of the substantial cost of acquisition and operation.

In accordance with the present invention, the various embodiments of the cameras 10A–C are relatively simple in structure and may be worn by the patient 14 for extended exposure time periods for determining qualitatively the existence, location, and general configuration of the radiation source 12, or tumor.

Accordingly, after administering the radioactive agent to the patient 14, the agent accumulates at the radiation source 12 which, in the exemplary embodiment illustrated in FIG. 2, is within the right eye 14a of the patient 14. The blindfold camera 10A is suitably affixed on the patient 14 adjacent to the examination site, which in this case is the right eye 14a, as shown in FIGS. 1 and 2. Since the camera 10A is flexible, it may be flexed for following the arcuate contour of the skin 14f at the examination site in substantially abutting contact with the skin 14f. As shown in FIG. 2, the camera 10A wraps tightly around the front of the patient's head 14b over both eyes and rearwardly along both temples generally adjacent to both ears 14d. The blindfold camera 10A has a suitable notch which is positioned over the nose 14c as illustrated in FIG. 1, with the first strap 16a shown in FIG. 2 ensuring a snug fit of the camera 10A around the patient's head 14b. In this way, the camera frame 20 is removably affixed to the patient 14 at the examination site for allowing the patient mobility to carry or wear the frame 20 for the predetermined exposure time period for an extended examination as desired.

As shown for example in FIG. 4, the distance of the film 24 from the radiation source 12 is indicated by the length R, and the exposure of the film 24 is related to the reciprocal of the distance squared (i.e., $1/R^2$) which, therefore, means that the closer the film 24 is to the source 12, the better will be the exposure and, therefore, the better the sensitivity or resolution of the image formed by the source 12. Since the blindfold camera 10A is flexible and the window 22 may be pressed against the patient's skin 14f, the resolution of the image from the source 12 on the film 24 is maximized over that which would be obtained if the window 12 were spaced apart from, and not allowed to abut the skin 14f. Accordingly, the sensitivity of the cameras 10 for conventional gamma ray or x-ray detection from the source 12 may be on the order of 10–1000 times higher than that of conventional (non-film) gamma cameras.

Furthermore, since the cameras 10 are relatively lightweight and are portable, they may be worn by the patient 14 for extended exposure time periods including for example, periods greater than about 10 hours and up to about 100 hours, or several days, or up to 1–2 weeks as desired. This is about 20–200 times higher than that practiced in imaging with conventional gamma cameras. As a result of the increased sensitivity and exposure time indicated above, the number of gamma or x-ray events detected will be about 200 to about 200,000 times higher than that obtained with conventional gamma cameras. As a result, small malignant neoplasms or tumors may be detectable with this method at very early stages.

Referring again to the exemplary portion of the camera 10 illustrated in FIG. 4, the window 22, film 24, and screen 26 are in the form of respective parallel sheets layered together and bound together around the perimeters thereof by the frame 20. They are flexible with the frame 20 around at least one bending axis for substantially matching the examination site contour in at least one respective axis of curvature thereof. For example, FIG. 2 illustrates a horizontal plane through the patient's head 14b at the general elevation of the eyes, with the blindfold camera 10A being flexible at least in this one plane. In the preferred embodiment, the window 22, film 24, and screen 26 are also flexible with the frame 20 around at least two orthogonal or perpendicular bending axes for substantially mapping the examination site contour in two directions. As shown in FIG. 1, the elevation of the head 14b has some curvature thereto, with the blindfold camera 10A also being flexible in this vertical direction so that the window 22 again may be maintained in abutting contact with the patient's skin 14f in two directions in the vicinity of the eyes 14a.

Referring again to FIG. 4, this exemplary camera 10 includes a pair of the screens 26 adjoining the film 24 on opposite sides thereof. The screens 26 are followed in turn by a respective pair of resilient, conforming foam sheets 30 which are provided to press the respective screens 26 firmly against the opposite sides of the film 24. Following in turn the foam sheets 30 are a pair of respective opaque sheets 32 which prevent light leakage upon the film 24 and make the camera light-tight, since the film is sensitive to visible light.

Figure 5:
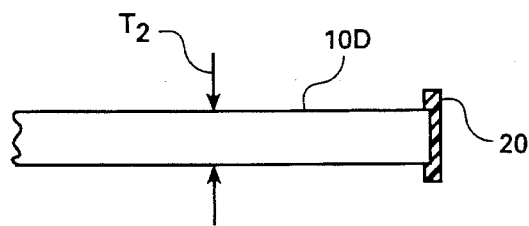
FIG. 5 illustrates a portion of a nuclear medicine camera which is identical to the embodiment illustrated in FIG. 4 except that it does not include a collimator therein.

In the exemplary embodiment illustrated in FIG. 4, the camera 10 further includes a suitable, flexible collimator 34 in sheet form which is disposed between the bottom screen 26 and the window 22 within the perimeter of the frame 20. The collimator 34 is effective for receiving the radioactive decay particles at preselected acceptance or incidence angles, and is flexible with the frame 20 around at least the one bending axis, and preferably both bending axes, for matching the examination site contour. The various embodiments of the cameras 10 may include the collimator 34 illustrated in FIG. 4, or may exclude the collimator 34 as illustrated schematically in FIG. 5. There are various advantages and disadvantages associated with the collimator 34, with the elimination of the collimator 34 as shown in FIG. 5 resulting in a camera designated 10D having a thickness $T_2$ which is correspondingly thinner than the camera 10 illustrated in FIG. 4 having a thickness $T_1$ which includes the collimator 34. As indicated above, it is desirable to position the film 24 as close as possible to the radiation source 12 since resolution increases quadratically as the film 24 is positioned closer to the source 12.

Two different types of the camera may therefore be used, one being collimated and the other being uncollimated. The choice will depend on the type of radiation being detected and on whether the imaging information required is a simple "yes/no" answer about the possible presence of a tumor. The uncollimated camera can be used to detect energetic beta particles, which heretofore are not known to have been used in human diagnostic testing, and has higher sensitivity since the film may be positioned closer to the radiation source. The uncollimated camera has lower spatial resolution when used for the detection of gamma rays and x-rays than the collimated camera, with the difference being on the order of 100-fold or more. The uncollimated camera will provide only a very rough image of the lesion or tumor. The collimator 34 may take any conventional form including parallel-hole types which allow detection of gamma or x-rays impinging perpendicularly to the collimator's surface within a small acceptance angle. Other types of collimators may also be used including diverging, converging, slant hole, and fan beam types. The collimator is generally of high sensitivity, particularly with relatively short holes to reduce the distance between the radiation source and the film.

Referring again to FIG. 4, the components of the camera 10 may be formed from suitable modifications of conventional x-ray type film plates having the required flexibility. The camera 10 may be constructed as shown in FIG. 4 for providing symmetry of construction about the film 24 for receiving radiation from either side thereof as desired, or may be specifically configured for receiving radiation from one side only. The frame 20, window 22, foam sheets 30, and opaque sheets 32 may be formed of suitable synthetic resins or plastics for example.

For gamma and x-rays, the thickness and type of the scintillation screen 26 will depend on the characteristic energy of the gamma or x-rays emitted from the radioactive agent or isotope, with suitable scintillator materials including higher atomic number (higher Z) being used for higher emitted photon energies. High atomic-number elements are preferred for enhancing the efficiency of conversion of the radioactive decay particles into photons of radiation such as visible light to which the photographic file 24 is preferentially sensitive. Scintillator screens and scintillator materials are well known and may be conventionally chosen for use in the various embodiments of the cameras 10 in the present invention. For example, the scintillation screen 26 may be formed of a preselected scintillation material and may be suitably sized in thickness for preferentially receiving and converting gamma rays and/or other ionizing radiation energy to produce the photographic-film exposure image. The scintillation screen 26 may be correspondingly configured for also receiving and converting x-rays in an optimum manner.

The cameras 10 now allow the detection of conventional beta particles or rays which, of course, is not available in conventional gamma cameras. Since beta particles are readily scattered, it is desirable to have the camera 10 as thin as possible, and therefore the collimator 34 is not used. The components of the camera 10 should be made as thin as possible for maximizing the detection of the short ranged beta particles from the radiation source 12. The scintillation screen 26 may therefore be specifically configured for receiving and converting the beta rays to produce the exposure image.

The various cameras 10 may be suitably tailored in shape, size, and collimator design to the specific application including the organ or site to be imaged, the specific radioactive isotope, the type of lesion or tumor to be detected, and the specific radioactive agent such as conventional radiopharmaceutical agents, as well as radio-labeled monoclonal antibodies. Since relatively long exposure times may now be practiced with relatively small amounts of radioactivity, the use of relatively long-lived isotopes such as radioactive iodine $^{125}$I, which has a half-life of about 60 days, or other such isotopes not currently used in clinical nuclear medicine may then be used.

As indicated above, the collimator 34 may take any suitable configuration with suitable contour following flexibility with individual collimator segments or cells 34a being as short as practical to reduce the distance R between the source 12 and the positioned film 24. The collimator 34 may be made of lead, although tungsten is preferred for compactness. The individual cells 34a may be about 1 cm by 1 cm in section or larger with the cells being circular, square, rectangular, or any other suitable configuration.

Figure 7:
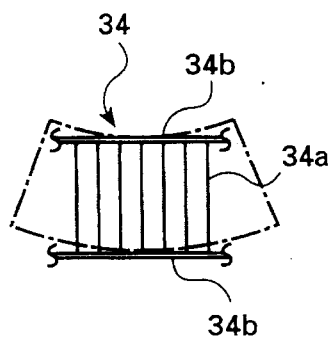
FIG. 7 is an exemplary embodiment of the collimator illustrated in FIG. 4 having flexible outer and inner bands allowing flexing of individual collimator cells.

One exemplary method of providing flexibility in the collimator 34 is by joining adjacent rigid cells 34a together using suitable flexible joints or hinges. For example, FIG. 7 illustrates one embodiment of the collimator 34 which is a mosaic-type assembly of small parallel-hole collimator cells 34a positioned side by side. The entire set of cells 34a is suitably held between two flexible bands or sheets 34b that act as a collimator housing. Flexing of the collimator 34 stretches the flexible sheet 34b to allow articulation or curvature for following the patient's skin. The collimator 34 may flex along two or more orthogonal bending axes in either of opposite positive and negative bending directions, i.e., up or down. Since the collimator 34 is also held within the camera frame 20 as illustrated in FIG. 4, it flexes along therewith.

Figure 8:
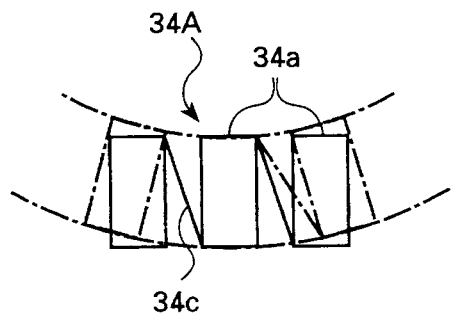
FIG. 8 is a schematic representation of the collimator of FIG. 4 in accordance with another embodiment wherein adjacent collimator cells are hinged together for providing flexibility of the collimator.
Figure 9:
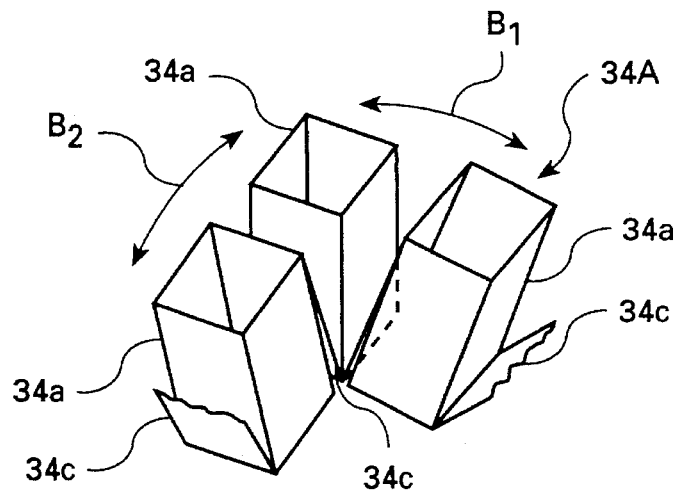
FIG. 9 is a schematic representation of three adjacent collimator cells of the exemplary embodiment illustrated in FIG. 8 providing hinging in two directions so that the collimator is flexible in two orthogonal axes.

FIG. 8 illustrates schematically another embodiment of the collimator designated 34A in which the adjoining individual cells 34a are rigid and articulated together by hinges 34c which are preferably plastic. In this way, the individual cells 34a may rotate relative to adjacent cells 34a for providing flexibility of the collimator 34A. FIG. 9 illustrates the flexibility of the collimator 34A in more particularity with three adjoining cells 34a being illustrated for example. Each of the hinges 34c is joined at the top of one cell and the bottom of an adjacent cell for allowing articulation either upwardly or downwardly of the adjacent cells. The hinges 34c are provided on the adjacent sides of the individual cells 34a to allow bending of the collimator 34A around two orthogonal or perpendicular bending axes as represented by bending directions $B_1$ and $B_2$ which provide suitable flexibility for substantially matching the examination site contour. For the general two-axis bending geometry illustrated in FIG. 9, the collimator cells 34a are preferably square in configuration, although other configurations may also be used.

Figure 10:
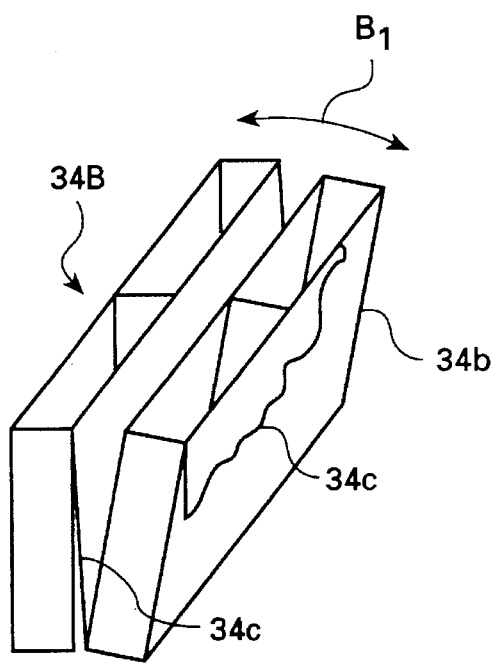
FIG. 10 is a schematic representation of adjacent cells in a collimator in accordance with another embodiment of the present invention wherein the cells are generally rectangular and are flexible in only one direction along the longitudinal axis thereof.

FIG. 10 illustrates another embodiment of the collimator designated 34B which is configured for bending solely about one bending axis, e.g. the $B_1$ direction, and therefore the collimator cells, designated 34b, are preferably rectangular in configuration with the long sides thereof being parallel to the bending axis for allowing simple one-axis cylindrical bending of the collimator 34B. The hinges 34c may be made of the same material or metal as the collimator 34B itself, or may be a suitable other material such as plastic.

Figure 6:
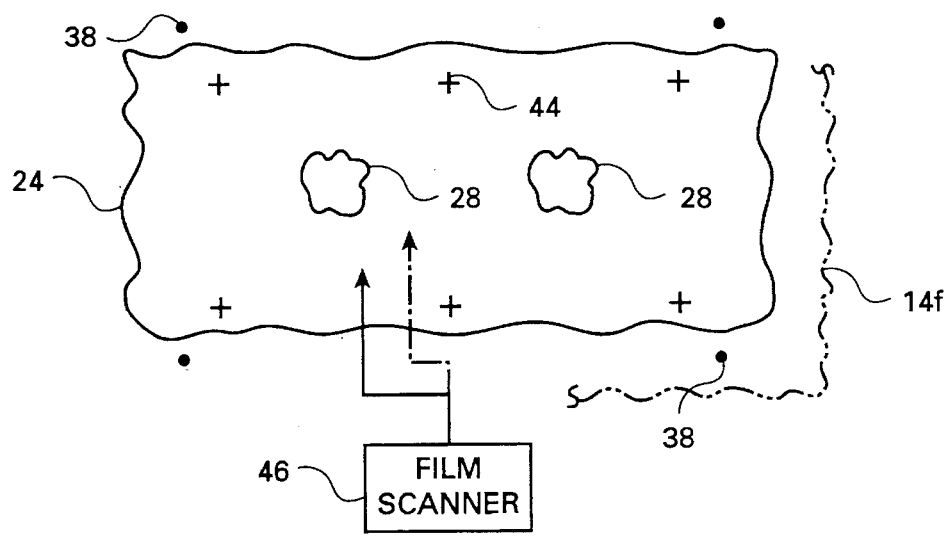
FIG. 6 is a planar view of a portion of exposed and developed film from the camera embodiment illustrated for example in FIGS. 2 and 4 showing multiple exposure image projections of the radiation source.

As indicated above, any suitable configuration for the various collimator cells 34a,b may be used and suitably sized in height and area for optimally receiving either gamma rays, or x-rays, for example, to produce the exposure image 28 shown in FIG. 6 for example. The gamma ray or x-ray penetration through the junctions or hinges 34c between the collimator cells 34a,b can be discounted by a trained radiologist during the visual evaluation of the raw exposure image, or may be removed by a suitable computer routine from a digitized derivative of the image itself.

More specifically, the flexible camera such as the blindfold camera 10A illustrated in FIG. 2 allows the film 24 to wrap around an arcuate portion of the examination site over the radiation source 12 or tumor therein. The film 24 therefore can follow the examination site contour over at least an acute included angle up to about 90°, or more, for providing multiple image projections of the source 12 on the film 24. Without the use of the collimator 34, the exposure image 28 will be substantially continuous and decrease in intensity as the distance from the source 12 increases. By using the collimator 34, the incident radiation is accepted only along the axes of the individual cells providing multiple image projections with the wrap-around film 24 as shown in FIG. 6. Accordingly, these multiple image projections may be used for accurately locating the actual position of the source 12 inside the patient by correlating the location of the images 28 relative to the position of the film 24 over the patient's examination site.

Figure 11:
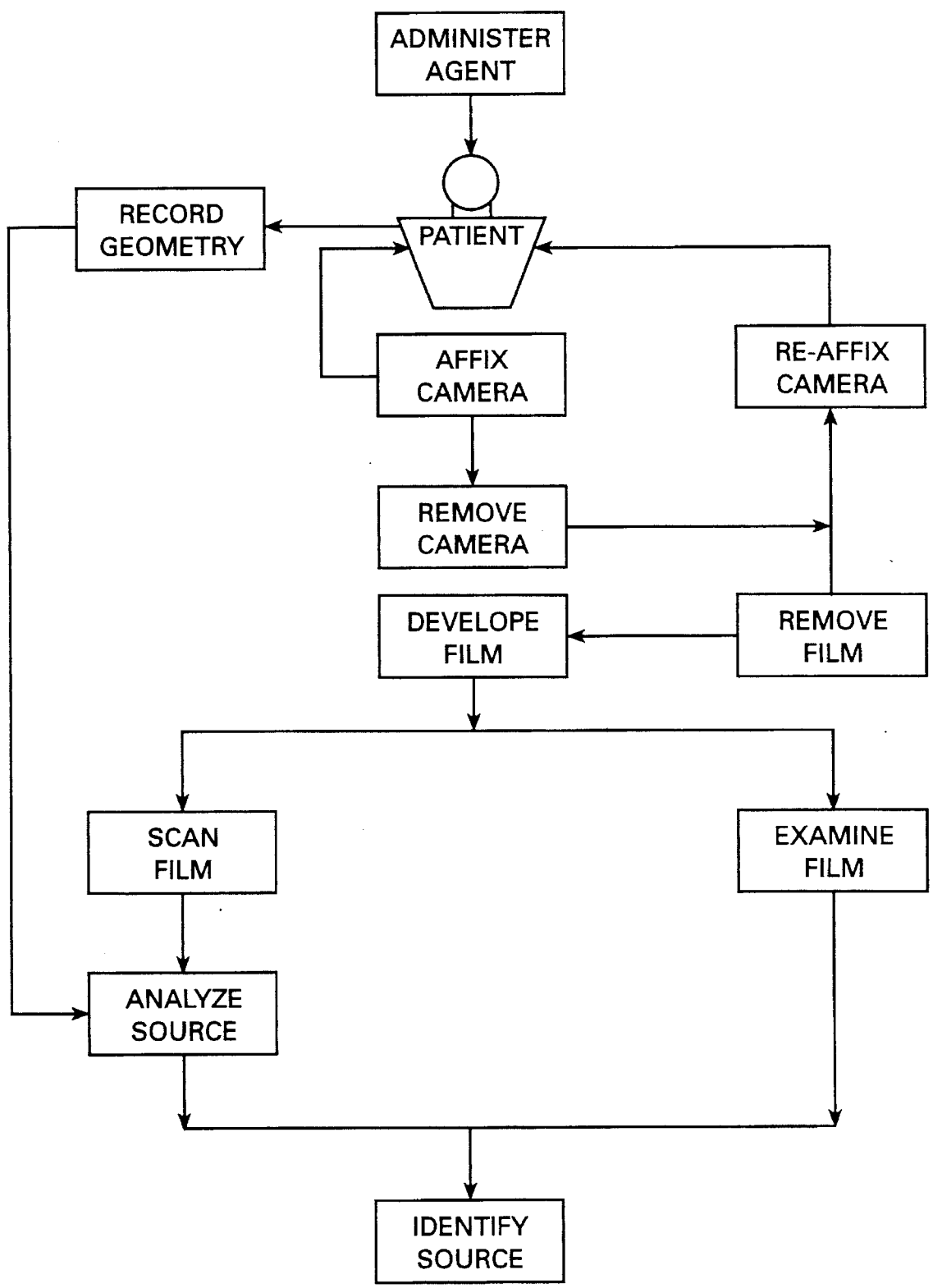
FIG. 11 is a flow chart of an exemplary method of using the flexible camera for identifying the radiation source within the patient.

More specifically, FIG. 11 is a flow chart representation of an exemplary method of using any of the various cameras 10 for the detection of shallow lesions or tumors evidenced by emissions from the radioactive source 12 within the patient 14. The patient 14 is conventionally administered either orally or by injection the desired radioactive agent such as a radiopharmaceutical agent or radio-labeled monoclonal antibody. These agents may be chosen for emitting gamma rays or x-rays, or even beta particles or rays for exposing the photographic film 24. The radioactive agent is conventionally selected for accumulating at the site of suspected lesions or tumors within the patient such as tumors of the eye, thyroid, or organs of the abdomen represented in FIG. 1 for example. A suitable form of the flexible photographic camera 10 is suitably removably affixed to the corresponding examination site on the patient such as the blindfold camera 10A covering the patient's eye; the belt camera 10B surrounding the patient's abdomen; or the patch camera 10C covering the front of the patient's neck or site of the thyroid gland. In all cases, the camera flexes to follow the contour of the patient's skin in abutting contact therewith.

The camera is then maintained affixed on the patient for a predetermined examination or exposure time period so that radiation decay particles expose the film 24 in the camera to form an exposure image of the radiation source 12. A particular advantage of the present invention is that the camera 10 is portable on the patient, i.e. worn by the patient, for allowing mobility of the patient during the examination period. The examination or exposure period is suitably selected in duration and may be greater than about ten (10) hours and up to about one hundred (100) hours, for example, for providing early detection of small tumors which is a substantial improvement over conventional gamma cameras which provide relatively short examination periods.

Another advantage of the present invention is that the camera 10 may be temporarily removed from the patient for various practical reasons and then reaffixed on the patient at the same examination site for continuing exposure of the film therein. In order to accurately reaffix the camera over the examination site, the various cameras illustrated in FIG. 1 preferably also include a plurality of alignment points 36 in the exemplary form of short line markings which are spaced around the respective camera frames 20 for being aligned with a respective plurality of registration or fiducial marks 38 temporarily drawn or made on the patient's skin 14f for aligning the camera 10 and in turn the film 24 therein over the examination site. In this way, the camera 20 may be removed and reaffixed accurately by aligning the points 36 on the camera with the marks 38 on the patient.

Referring again to FIG. 11, once the required exposure period has ended, the camera may be finally removed from the patient and disassembled as required for removing the film 24 therefrom. And then the film is conventionally developed to obtain the exposure image 28 thereon.

FIG. 6 illustrates exemplary multiple images 28 on the developed film 24 relative to exemplary registration marks 38 on the patient. As FIG. 11 indicates, the developed film 24 may be itself examined by a suitably trained radiologist to visually examine the film to ascertain the significance of the image 28 for medical diagnostic purposes.

The image 28 may be more fully examined or analyzed using a suitable computer to recreate the contour of the radiation source 12 and its relative position within the patient 14. The geometry of the patient at the desired examination site is suitably obtained or recorded by a conventional geometry scanner or digitizer 40 as shown schematically in FIG. 1 which provides the spatial coordinates of the various external registration marks 38. Alternatively, a conventional computerized axial tomography (CAT) scanner 42 also shown schematically in FIG. 1 may be used for the same purpose to accurately record the geometry of the patient at the desired examination site both externally and internally.

As shown in FIG. 6, the film 24 also preferably includes a plurality of suitable reference points 44 (in cross form for example) to provide a geometric reference for accurately locating the exposure image 28 relative to the reference points 44 which in turn is relative to the alignment points 36 on the camera and in turn relative to the registration marks 38 on the patient 14 (shown in phantom). The film 24 may then be conventionally scanned using a suitable film scanner or digitizer 46 shown schematically in FIG. 6 which digitizes the location coordinates of the image 28 thereon. A suitable computer is used for analyzing the source data which compares the scanned image 28, and its multiple projections if any, relative to the recorded geometry of the examination site for analyzing the source 12 for the identification thereof. Identification of the source 12 may include its general outer configuration and size, and its general location within the patient as defined in two or three dimensions. In this way, the nature and location of the radiation source 12 as shown in FIG. 2 for example may be determined for identifying a suspected lesion or tumor thereat.

Since the camera of the present invention is relatively simple in construction and use, it is intended to provide primarily qualitative general information for the early detection of suspected lesions or tumors at shallow depths not deeper than about 3 cm within the patient. In order to improve the evaluation of the radioactive source or tumor, the various embodiments of the cameras 10 preferably are configured with left and right symmetry such as shown for the blindfold camera 10A so that the radiation source 12 in the right eye may also be evaluated relative to any left eye image which provides a reference of normal tissue.

Accordingly, the various embodiments of the camera disclosed above have suitable flexibility for being attached to the patient's skin to follow the shape and curvature of the body to place the film as close as possible to the underlying radiation source for improving recording thereof. Since the camera may extend over the sides of the examination site for viewing the radiation source from at least two views which may be generally perpendicular to each other, the camera is able to provide three dimensional information of the source including depth thereof inside the patient. The camera may be used with or without the segmented collimator 34 as desired. The collimator 34 can provide better spatial resolution of the source but decreases the sensitivity since the film is necessarily positioned further away from the radiation source. Without the collimator 34, lower spatial resolution is expected, but at higher detection sensitivity in view of the closer position of the film to the radiation source.

The camera may be designed in a variety of geometries for specific applications with specific organs such as the eyes, face, head, thorax, abdomen, limbs, and pelvis. The cameras may be as small as a few square centimeters, or as large as the entire trunk. And, the exposure time, depending on the radiopharmaceutical used and on the application, may vary from tens of minutes to several days as desired. In the case of detecting breast cancer, for example a small, previously undetected breast cancer, the camera may be formed in the shape of a conventional brassiere with a pair of generally conical cups having a suitable cross section like that illustrated in FIG. 4 for placing the film closely adjacent to the skin surface for detecting the early stages of possible breast cancer.

While there have been described herein what are considered to be preferred and exemplary embodiments of the present invention, other modifications of the invention shall be apparent to those skilled in the art from the teachings herein, and it is, therefore, desired to be secured in the appended claims all such modifications as fall within the true spirit and scope of the invention.

Accordingly, what is desired to be secured by Letters Patent of the United States is the invention as defined and differentiated in the following claims;

We claim:

1. A nuclear medicine camera 10 for photographically recording radioactive decay particles emitted from a source 12 inside a patient 14 comprising:

a frame 20 containing a window 22, a photographic film 24, and a scintillation screen 26 disposed adjacent thereto for emitting secondary radiation to form a photographic exposure image 28 on said film 24 upon reception through said window 22 of said radioactive decay particles from said source 12 inside said patient 14, said window 22, film 24 and scintillation screen 26 each being in the form of respective sheets layered together and bound together around perimeters thereof by said frame 20, and being flexible with said frame 20 around at least one bending axis for substantially matching said examination site contour in at least one axis of curvature thereof; and further comprising a collimator 34 disposed between said screen 26 and said window 22 for receiving said radioactive decay particles at preselected acceptance angles and being flexible with said frame 20 around at least said one bending axis for matching said examination site contour; said collimator comprising a plurality of individual cells 34a,b articulated together for effecting said flexibility thereof, and each said cell having an axis along which incident radiation from the examination site is accepted within one of said preselected acceptance angles.

2. A camera according to claim 1 wherein said scintillation screen 26 is formed of a scintillation material preselected for receiving and convening beta rays to produce said exposure image.

3. A camera according to claim 1 wherein said collimator cells 34a,b are sized and configured for receiving gamma rays to produce said exposure image.

4. A camera according to claim 1 wherein said collimator cells 34*a,b* are sized and configured for receiving x-rays to produce said exposure image.

5. A camera according to claim 1 wherein said collimator 34 is flexible around two orthogonal bending axes for substantially matching said examination site contour.

6. A camera according to claim 1 in the form of a blindfold 10A wearable by said patient 14 over at least one eye 14*a* thereof forming said examination site, and being removably affixed to the head 14*b* of said patient 14 by being wrapped substantially around said head 14.

7. A camera according to claim 1 wherein said film 24 follows said examination site contour over at least an acute included angle for providing multiple image projections of said source 12.

8. A camera according to claim 1 in the form of a belt 10B wearable by said patient 14 around the trunk 14*e* thereof forming said examination site, and being removably affixed thereto by a strap 16*b* joining ends of said belt 10B together.

9. A camera according to claim 1 in the form of a patch 10C wearable by said patient 14 over a selected area of said skin 14*f*, and being removably affixed thereto by an adhesive 18.

10. A camera according to claim 1 further comprising a plurality of alignment points 36 spaced around said frame 20 for being aligned with a respective plurality of registration marks 38 on said patient's skin 14*f* for aligning said film 24 over said examination site.

11. A method of photographically recording radioactive decay particles emitted from a source 12 inside a patient 14 comprising:

administering a radioactive agent into said patient 14 selected for accumulating at said source 12 inside said patient 14 for emitting said radioactive decay particles therefrom;

affixing a flexible photographic camera containing a photographic film 24, a scintillator screen 26 and a collimator 34 on said patient 14 adjacent to an examination site, with said collimator being disposed between said screen 26 and said patient 14, and said camera 10 being flexible for following an arcuate contour at said site in substantially abutting contact therewith; and maintaining said camera affixed on said patient for a predetermined exposure time period so that radioactive decay particles expose said film in said camera to form an image of said source, with said camera being portable on said patient for allowing mobility of said patient during said exposure period.

12. A method according to claim 11 wherein said agent is a radiopharmaceutical agent.

13. A method according to claim 11 wherein said agent is a radio-labeled monoclonal antibody.

14. A method according to claim 13 wherein said antibody is effective for emitting beta particles for exposing said film.

15. A method according to claim 11 wherein said exposure period is greater than about ten hours and up to about 100 hours.

16. A method according to claim 11 further comprising:

providing registration marks 38 on said patient skin 14*f*; and providing alignment points 36 on said camera 10 and aligning said points 36 with said registration marks 38.

17. A method according to claim 16 further comprising:

temporarily removing said camera 10 from said patient 14; and reaffixing said camera 10 on said patient 14 at said examination site by aligning said points 36 and respective marks 38.

18. A method according to claim 16 further comprising:

providing reference points 44 on said film 24;

recording geometry of said patient 14 at said examination site;

removing said camera from said patient after said exposure period;

removing said film from said camera and developing said film to obtain said image;

scanning said developed film for digitizing location of said image 28 thereon; and comparing said scanned image 28 relative to said recorded geometry of said examination site to analyze said source 12 for identification thereof.

19. A method according to claim 18 wherein said geometry recording step is accomplished using a computerized axial tomography (CAT) scanner 42.

* * * * *